US007244424B2

(12) United States Patent
Mikelsaar et al.

(10) Patent No.: US 7,244,424 B2
(45) Date of Patent: Jul. 17, 2007

(54) **STRAIN OF MICRO-ORGANISM *LACTOBACILLUS FERMENTUM* ME-3 AS NOVEL ANTI-MICROBIOL AND ANTI-OXIDATIVE PROBIOTIC**

(75) Inventors: Marika Mikelsaar, Tartu (EE); Mihkel Zilmer, Tartu (EE); Tiiu Kullisaaar, Tartu (EE); Heidi Annuk, Tartu (EE); Epp Songisepp, Pölva (EE)

(73) Assignee: University of Tartu, Tartu (EE)

( * ) Notice: Subject to any disclaimer, the term of this patent is extended or adjusted under 35 U.S.C. 154(b) by 0 days.

(21) Appl. No.: 10/481,713

(22) PCT Filed: Jun. 21, 2002

(86) PCT No.: PCT/EE02/00006

§ 371 (c)(1),
(2), (4) Date: Dec. 22, 2003

(87) PCT Pub. No.: WO03/002131

PCT Pub. Date: Jan. 9, 2003

(65) Prior Publication Data

US 2004/0151708 A1 Aug. 5, 2004

(30) Foreign Application Priority Data

Jun. 29, 2001 (EE) ................................ 200100356

(51) Int. Cl.
*A61N 63/00* (2006.01)
(52) U.S. Cl. .................. 424/93.45; 424/93.1; 435/243; 435/252.9
(58) Field of Classification Search ............. 435/252.9, 435/243, 853, 170, 41; 424/93.45
See application file for complete search history.

(56) References Cited

U.S. PATENT DOCUMENTS

| | | | | |
|---|---|---|---|---|
| 5,176,911 | A * | 1/1993 | Tosi et al. ................. | 424/93.45 |
| 6,180,100 | B1 * | 1/2001 | Bruce et al. .............. | 424/93.45 |
| 6,342,366 | B1 * | 1/2002 | Dondi et al. ................... | 435/32 |
| 6,479,051 | B1 * | 11/2002 | Bruce et al. .............. | 424/93.45 |

FOREIGN PATENT DOCUMENTS

RU        2133272        7/1999

OTHER PUBLICATIONS

"Infection" Dictionary.com, accessible at http://dictionary.reference.com/search?q=infection accessed on Dec. 14, 2005.*
Mikelsaar, Marika, et al., "Antagonistic and Antioxidative Activity of Lactobacilli and Survival in Oxidative Milieu, American Journal of Clinical Nutrition", vol. 73, No. 2S, Feb. 2001, p. 495S.
Sepp E., et al., "Intestinal Microflora of Estonian and Swedish Infants", ACTA Paediatrica, vol. 86, No. 9, 1997, pp. 956-961.
Kullisaar, T., et al., "Two Antioxidative Lactobacilli Strains as Promising Probiotics", International Journal of Food Microbiology, vol. 72, No. 3, 2002, pp. 215-224.
Mikelsaar, M., et al., "Intestinal Lactobacilli of Estonian and Swedish Children", Microbial Ecology in Health and Disease, vol. 14, No. 2, Jun. 2002, pp. 75-80.
Annuk, H., et al., "Characterisation and Diferentiation of Lactobacilli by Lectin Typing", Journal of Medical Microbiology, vol. 50, No. 12, Dec. 2001, pp. 1069-1074.
Songisepp, E. et al., "A New Probiotic Cheese With Antioxidative and Antimicrobial Activity", *Journal of Dairy Science*, vol. 87, No. 7, 2004, pp. 2017-2023.
Sepp, E. et al., "Intestinal Microflora of Estonian and Swedish Infants", *Acta Paeditrica*, 86, 1997, pp. 956-961.
Agostini, C. et al., "Probiotic Bacteria in Dietetic Products for Infants: A Commentary by Espghan Committee on Nutrition", *Journal of Pediatric Gastroenterology and Nutrition*, vol. 38, No. 4, 2004, pp. 365-374.
Mukai, T. et al., "Inhibition of Binding of *Helicobacter pylori* to the Glycolipid Receptors by Probiotic *Lactobacillus reuteri*", *FEMS Immunology and Medical Microbiology*, vol. 32, 2002, pp. 105-110.
Ringel, Y. et al., "The Brain, the Gut, the Food, and the Bacteria? Update on Treatment of Functional Gastrointestinal Disorders", *Medscape from WebMD, MedGenJournal*, Dec. 23, 2004.
Fedorak, R. et al., "Probiotics and Prebiotics in Gastrointestinal Disorders", *Medscape from WebMD, Curr Opin Gastroenterol*, vol. 20(2), 2004, pp. 146-155.
Reid, G. et al., "Potential Uses of Probiotics in Clinical Practice", *Clinical Microbiology Reviews*, Oct. 2003, pp. 658-672.
Umezawa, K. et al., "Granulation in Livers of Mice Infected With *Salmonella typhimurium* is Caused by Superoxide Released From Host Phagocytes", *Infection and Immunity*, vol. 63, No. 11, Nov. 1995, pp. 4402-4408.
Suzuki, H. et al., *Helicobacter pylori*-Associated Gastric Pro- and Antioxidant Formation in Mongolian Gerbils, *Free Radical Biology & Medicine*, vol. 26, Nos. 5/6, 1999, pp. 679-684.
Storz, G. et al., "Oxidative Stress", *Current Opinion in Microbiology*, vol. 2, 1999, pp. 188-194.
Tseng, H. et al., "Accumulation of Manganese in *Neisseria gonorrhea* correlates With Resistance to Oxidative Killing by Superoxide Anion and is Independent of Superoxide Dismutase Activity", *Molecular Biology*, vol. 40(5), 2001, pp. 1175-1186.
Archibald, F. et al., "Manganese and Defenses Against Oxygen Toxicity in *Lactobacillus plantarum*", *Journal of Bacteriology*, vol. 145, No. 1, Jan. 1981, pp. 442-451.

(Continued)

*Primary Examiner*—Leon B Lankford, Jr.
*Assistant Examiner*—Allison M. Ford

(57) ABSTRACT

The strain of micro-organism *Lactobacillus fermentum* ME-3 is a novel anti-microbial and anti-oxidative probiotic. It has a high anti-microbial effect on *Escherichia coli, Shigella sonnei, Staphylococcus aureus, Salmonella typhimurium*, and moderate activity against *Helicobacter pylori* strains. The strain of micro-organism possesses Mn-superoxide dismutase and both its lysates and intact cells have high anti-oxidative activity, increasing the glutathione redox ratio in blood sera and able to capture toxic hydroxyl radicals. The strain of micro-organism could be used as a probiotic for the production of functional food (yoghurt, cheese) and non-comestibles (tablets, capsules) for the prophylaxis of intestinal and uroinfections, both for the prevention and treatment of chronic diseases, caused by prolonged oxidative stress.

5 Claims, No Drawings

OTHER PUBLICATIONS

Seib, K. et al., "Defenses Against Oxidative Stress in *Neisseria gonorrhea* and *Neisseria meningitidis*: Distinctive Systems for Different Lifestyles", *The Journal of Infection Diseases*, vol. 190, 2004, pp. 136-147.

Kullisaar, T. et al., "Two Antioxidative Lactobacilli Strains as Promising Probiotics", *International Journal of Food Microbiology*, vol. 72, 2002, pp. 215-224.

Truusalu, K. et al., "The Influence of Antibacterial and Antioxidative Probiotic Lactobacilli on Gut Mucosa in a Mouse Model of *Salmonella* Infection", *Microbial Ecology in Health and Disease*, vol. 16, 2004, pp. 180-187.

Mikelsaar, R. et al., B-1699 Probiotic Lactobacilli Enhance Eradication of *Salmonella typhimurium* in Animal Model, *44th Interscience Conference on Antimicrobial Agents and Chemotherapy* (Abstract), Oct. 30-Nov. 2, 2004, p. 61.

Cherbut, C. et al., "The Prebiotic Characteristics of Fructooligosaccharides are Necessary for Reduction of TNBS-Induced Colitis in Rats", *The American Society For Nutritional Sciences, J. Nutr.*, vol. 133, Jan. 2003, pp. 21-27.

Product Brochure, Hellus, AS Tallinna Piim (Tallinn Dairy Ltd.) date unknown.

Mikelsaar, M. et al., "Human Lactic Acid Microflora and its Role in the Welfare of the Host", *Lactic Acid Bacteria Microbiological and Functional Aspects*, Third Edition, Marcel Dekker, Inc. 2004, pp. 453-505.

Annuk, H. et al., "Characterization of Intestinal Lactobacilli as Putative Probiotic Candidates", *Journal of Applied Microbiology*, vol. 94, 2003, pp. 403-412.

Mikelsaar, M. et al., "Intestinal Lactobacilli of Estonian and Swedish Children", *Microbial Ecology in Health and Disease*, vol. 14, 2002, pp. 75-80.

Kullisaar, T. et al., "Antioxidative Probiotic Fermented Goats' Milk Decreases Oxidative Stress-Mediated Atherogenicity in Human Subjects", *British Journal of Nutrition*, vol. 90, 2003, pp. 449-456.

* cited by examiner

STRAIN OF MICRO-ORGANISM *LACTOBACILLUS FERMENTUM ME-3* AS NOVEL ANTI-MICROBIOL AND ANTI-OXIDATIVE PROBIOTIC

The instant application is a national stage entry of PCT/EE20/00006, filed on 21 Jun. 2002, which further claims priority to Estonian national application P200100356 filed 21 Jun. 2001.

TECHNICAL FIELD

The present invention relates to biotechnology and will be used as a novel probiotic applied in the production of functional food (yoghurt, cheese) and non-food preparations (tablets, capsules) for the prevention or treatment of different diseases.

BACKGROUND ART

Probiotics are living microbial food additives, that have beneficial effect on the microbiological balance of the intestine and human health. Probiotics are used as functional food. Functional food is foodstuff, consumed additionally to usual food and containing bio-preparations (incl. probiotics) or other components favourably influencing human health or decreasing disease risks. Probiotics are consumed as components of food (probiotic yoghurt or cheese) or non-food preparations (lyophilised microbial cultures).

Most of probiotics are lactic acid bacteria, mainly lactobacilli. Lactobacilli are non-pathogenic micro-organisms, colonising the human intestinal and urogenital tract from early childhood to old age. Nowadays, several commercial probiotic lactobacilli are successfully used, among which *Lactobacillus rhamnosus* GG (Saxelin M. *Lactobacillus* GG—a human probiotic strain with thorough clinical documentation. Food Rev Int 1997; 13:293-313) is the best known. Recently some new strains of lactobacilli have been described and patented, for example *L. reuterii* (Korea patent KR211529, C12N 1/20, Korea Institute Science Technology, 1999), isolated from animal organism and for this reason inappropriate for human usage.

Several strains of *Lactobacillus fermentum* are used for correction and stabilisation of intestinal micro-flora in case of dysbacterioses and urogenital infections with different ethiologies. The strain of micro-organism *Lactobacillus fermentum* 39 is used for producing the bacterial biological preparation (PCT/SU89/00264 (WO 91/05852), C12N 1/20, A61K 35/74, University of Tartu, 1991). The strain *Lactobacillus fermentum* 90-TS-4 (RU2133272, C12N 1/20, A61K 35/74, Akivo Lentsner et al., 1999) is characterised by lectin typing as a mannose-sensitive profile of the cell wall. The preparation is prescribed for use in gynaecology.

There are some well-known probiotics, targeted against only one pathogen (for example Salmonella) (U.S. Pat. No. 5,478,557, A61K 35/74, US Agriculture, 1995; U.S. Pat. No. 5,340,577, A61K 35/74, US Army, 1994). Up to the present no strain of lactobacilli with an extensive anti-microbial effect against numerous pathogens and opportunistic pathogens has been described.

Likewise, yet no such strain of micro-organism is known that could have natural antibiotic resistance against drugs most frequently used in the treatment of infections. This property would permit to use such strains in case of antibiotic-treated patients. A set of different micro-organisms is used in veterinary, containing also one strain of *L. fermentum,* but this strain does not have a concurrent anti-microbial and anti-oxidative effect (RU2119796, A61K 35/66, Zakrõtoje aktsionernoje obshestvo "BAKS", 1998).

Anti-oxidative preparations like vitamin E and C, betacarotene a.o. nowadays get much attention in connection to healthy nutrition. Excessive formation of reactive oxygen species (ROS) in tissue respiration can cause the damage of cells and the course of tissues. The formation of active oxygen may depend on some stress factors, such as alcohol, peroxides, and some drugs.

Usually excessive oxidation is closely connected with nutritional diseases, age, arteriosclerosis, misfunctions of the central nervous system and the intestinal tract, cancer a.o. pathological conditions. An organism has several defence systems against the toxigenicity of oxygen. It is important to take anti-oxidative substances to guarantee the functioning of these systems.

Of known solutions, the closest to this invention is the patent describing anti-oxidative food, an anti-oxidative preparation and a method of antioxidation (EPO649603, A23L 3/3472, A23L 3/3571, Otsuka Pharma Co Ltd. 1995). The object of this invention is a preparation that contains a natural substance involving mangan (leaves of tea plant) and the micro-organism *Lactobacillus plantarum* that produces catalase and a superoxidase-dismutase system, thus increasing the anti-oxidative activity of the host organism. The authors of this invention declare that the preparation prevents diseases developing due to active oxygen. However, they do not describe the effect of particular Lactobacillus strain with a decreasing anti-oxidative activity or capturing hydroxyl radicals in vitro. Besides that, this strain of micro-organism is also imperfect because for getting the presumable anti-oxidative effect in an organism (in vivo), it is necessary to add some Mn-containing raw material (leaves of tea plant) to the preparation, because it is only in this case its SOD (superoxide dismutase) activity is realised.

DISCLOSURE OF THE INVENTION

The aim of this invention is to present the strain of micro-organism as a novel anti-microbial and anti-oxidative probiotic for use in pharmaceutical and food industry, also in medicine as an antibiotic-resistant preparation for the prophylaxis and treatment of gastrointestinal and uroinfections, and against oxidative stress.

The object of the investigation—the strain of microorganism *Lactobacillus fermentum* ME-3 was isolated from a faecal sample of a healthy child during a comparative study of the micro-flora of Estonian and Swedish children, using MRS (Oxoid) media and cultivating it in a $CO_2$ environment (Sepp et al., Intestinal microflora of Estonian and Swedish infants, Acta Paediatrica, 1997, 86, 956-961).

The strain of micro-organism *Lactobacillus fermentum* ME-3 was isolated by seeding the dilutions of the faeces of healthy one-year-old Estonian child ($10^{-2}$-$10^{-7}$ in phosphate buffer with 0.04% thioglycol acid; pH 7.2). The dilutions were seeded on freshly prepared MRS agar-media and cultivated at 37° C. in a $CO_2$ environment. The strain, which is the object of invention, was isolated from a $10^{-5}$ dilution on the basis of the characteristic morphology of colonies and cells. A provisional and more precise identification followed as described next. Using additional tests, the strain was selected from other lactobacilli isolated from the same child on the basis of its special properties.

The fact that the microbial strain *Lactobacillus fermentum* ME-3 originates from the intestinal tract of a healthy child proves its GRAS (generally recognised as safe) status, i.e. that this strain of micro-organism is harmless for human organism and it is suitable for oral application.

Cultural-morphological characteristics were determined after cultivating the strain on MRS agar and in MRS broth media (OXOID). Microbial cells are Gram-positive rods of regular shape located in parallel chains, nonspore, of medium thickness and different length (2×3-5 μm).

Physiological-biochemical characteristics: MRS broth was suitable for cultivating the microbial strain during 24-48 hours in a 10% $CO_2$ environment, after which homogeneous turbid growth occurred in the broth. The colonies of micro-organism on MRS agar are white, rounded, with a regular edging.

The optimal growth temperature is 37° C., it multiplies also at 45° C., but it does not grow at 15° C. The optimal growth environment is at pH 6.5.

The negative catalase test, gas production by fermentation of glucose, production of $NH_3$ from arginine, and lysozyme production are the main properties. During reproduction in milk it produces 1.07% of acid.

The strain with above-mentioned characteristics was identified on the basis of biochemical activity with API 50 CHL System (BioMerieux, France) kit as *Lactobacillus fermentum* (ID % 99.6, T 0.87, only 1 test contra). The following sugars and alcohols were fermented—ribose, galactose, D-glucose, D-fructose, D-mannose, esculine, maltose, lactose, melibiose, saccharose, D-raffinose, D-tagatose and gluconate.

The profile of the metabolites of *Lactobacillus fermentum* ME-3 was characteristic of heterofermentative metabolism, determinated by the gas chromatographic method (Hewlett-Packard model 6890). The profile of fermentation depended on environment of incubation: besides lactic and acetic acids a big amount of succinic acid was produced in a $CO_2$ environment, but in an anaerobic environment much of ethanol was produced in addition to the above-mentioned substances (Table 1). Both succinic acid and ethanol can strengthen the stable properties of the microbial strain in milk fermented by this strain.

TABLE 1

The concentration of acetic acid, lactic acid, succinic acid and ethanol (mg/ml) in MRS media in cultivation of *Lactobacillus fermentum* ME-3 in microaerophilic and anaerobic environment during 24 and 48 h.

| *Lactobacillus fermentum* | Lactic acid mg/ml | | Acetic acid mg/ml | | Succinic acid mg/10 ml | | Ethanol | |
|---|---|---|---|---|---|---|---|---|
| ME-3 | 24 h | 48 h | 24 h | 48 h | 24 h | 48 h | 24 h | 48 h |
| $CO_2$ environment | 10.6 | 11.1 | 0.8 | 0.9 | 1.84 | 1.95 | 9.8 | 7.5 |
| Anaerobic environment | 8.2 | 8.8 | 1.0 | 1.0 | 0.57 | 0.97 | 7.0 | 33.3 |

Molecular Identification

Molecular identification by ITS-PCR (internal transcribed spacer —polymerase chain reaction) using *Lactobacillus fermentum* ATCC 14931 as the reference strain verified the previous identification with API 50 CHL.

The micro-organism with the above-mentioned properties was deposited in Deutsche Sammlung für Mikroorganismen und Zellkulturen GmbH-s, the registration number of the deposite is DSM 14241 (19.04.2001).

Anti-microbial Activity

*Lactobacillus fermentum* ME-3 expresses a high anti-microbial effect on *Escherichia coli, Shigella sonnei, Staphylococcus aureus, Salmonella typhimurium* 1 and 2, and *Helicobacter pylori* strains in vitro (Table 2).

TABLE 2

Anti-microbial activity of strain *Lactobacillus fermentum* ME-3 on modified MRS-agar, in MRS broth and milk.

| *Lactobacillus fermentum* ME-3 | *Escherichia coli* | *Shigella sonnei* | *Staphylococcus aureus* | *Salmonella typhimurium* 1 and 2 | *Helicobacter pylori* |
|---|---|---|---|---|---|
| MRS-agar | Inhibition zone (mm) | | | | |
| $CO_2$/ anaerobic environment | 24/22 | 26/21 | 20/19 | 25.8/ 24.7 | 23.8/ 19.7 | 13.2/13.1 |
| MRS broth | Decrease of total count ($\log_{10}$) compared with initial count | | | | |
| | log 6.0 | Log 6.7 | log 0.8 | log 6.3 | log 3.8 | not determined |

TABLE 2-continued

Anti-microbial activity of strain *Lactobacillus fermentum* ME-3 on modified MRS-agar, in MRS broth and milk.

| Lactobacillus fermentum ME-3 | Escherichia coli | Shigella sonnei | Staphylococcus aureus | Salmonella typhimurium 1 and 2 | Helicobacter pylori |
|---|---|---|---|---|---|
| Milk | | Suppression after different interval of time (24–48 h) | | | |
| | 24 t | 32 t | 24 t | 32 t    48 t | not determined |

Using milk fermentation it was possible to show that pathogens inoculated into milk were killed in 24–48 h if milk was fermented with *Lactobacillus fermentum* ME-3. Such property of the strain could help to prevent the multiplication of pathogens in products (yoghurt, cheese) fermented by this strain, and prevent food infections. Organic acids and ethanol produced by *Lactobacillus fermentum* ME-3 could ensure the high anti-microbial effect of this microbe.

Resistance to Antibiotics

According to a disk-diffusion test (BBL Sensi disks) and an E-test (AB Biodisk, Solna) *Lactobacillus fermentum* ME-3 was resistant to metronidazole, ofloxacin, axtreonam, cefoxitin and TMP-SMX. This allows us to use the strain *L. fermentum* ME-3 as a preparation accompanying antibiotic treatment in case of intestinal and uroinfections.

Surface Structures of Microbial Cell

The carbohydrate profile of the surface structure of microbial cells of *Lactobacillus fermentum* ME-3 was determined by lectin typing. The strain of lactobacilli agglutinated with *Griffonia simplifolia* I lectin, which is specific to Gal and GalNAc ligands in the cell wall.

The strain *Lactobacillus fermentum* ME-3 did not react with the following other lectins: *Concanavalin ensiformis* (Con A), *Griffonia simplicifolia* II, *Arachis hypogaea* (PNA), *Vicia sativa* (VSA) and *Tritium vulgaris* (WGA).

Hence the special composition of the glycocalyx of the cell wall of Lactobacillus ME-3 became clear with lectin typing, it contained residues of galactose and N-acetyl-galactose-amine. These compounds act as adhesins for engaging the receptors of mucosa on the epithelial cells of the upper urinary tract.

This is a possibility for blocking the mannose-resistant pili of *Escherichia coli* that makes our strain applicable in the prophylaxis of urinary tract infections.

Anti-oxidative Properties

Lactobacilli were incubated in a MRS broth (Oxoid Ltd.) for 24 h and centrifuged at 4° C. (1500 rev/mm) for 10 min, the precipitate was washed with isotonic salt (4° C.) and resuspended in 1.15% KCl (Sigma, USA). The density of the suspension was $1.1 \times 10^9$ bacterial cells per $ml^{-1}$, read at $OD_{600}$. To get lysates, the cells were disrupted by sonification (B-12 Branson Sonic Power Company, Danbury, Conn.) in 35 vibrations $s^{-1}$ 10 min in an ice bath and then for 10 min at −18° C. The suspension was centrifuged at 4° C. 10000 g/r for 10 min and the supernatant was filtered (MILLEY-GS, sterile, 0.22 μm; Millipore S. A., 67 Moisheim, France) to get a cell-free extract. *Lactobacillus fermentum* ME-3 cells and lysate produced $H_2O_2$ in a remarkable amount (Table 3).

TABLE 3

Total anti-oxidative capacity of *Lactobacillus fermentum* strains ME-3 and E-338-1-1 (according to LA and TAS tests), hydrogen peroxide content, glutathione red-ox ratio and activity of superoxide dismutase.

| Properties | Lactobacillus fermentum ME-3 | Lactobacillus fermentum E-338-1-1 |
|---|---|---|
| | Intact cells | Intact cells |
| TAA in LA-test (%) | 29 ± 0.7 (n = 5) | 0 |
| TAS (mmol/L) | 0.16 ± 0.03 (n = 5) | 0 |
| $H_2O_2$ (μg/ml) | 31 ± 26 (n = 3) | 49 ± 20 (n = 3) |
| | Lysate of cells | Lysate of cells |
| LA-test (%) | 59 ± 3.8 (n = 5) | 0 |
| $H_2O_2$ (μg/ml) | 229 ± 37 (n = 4) | 137 ± 25 (n = 3) |
| TGSH | 12.5 ± 4.1 | 5.5 ± 3.0 |
| GSSG (μg/ml) | 2.59 ± 2.01 | 5.5 ± 2.4 |
| GSH (μg/ml) | 9.95 ± 3.30 | Marks |
| GSSG/GSH | 0.28 ± 0.17 | $0^e$ |
| SOD (U/mg protein) | 0.859 ± 0.309 (n = 3) | Not determined |

Explanations:
LA-test—linolenic acid test;
TAA—total anti-oxidative activity;
TAS—total anti-oxidative status;
GSSG—oxidized glutathione;
GSH—reduced glutathione;
GSSG/GSH—glutathione red-ox ratio;
SOD—superoxide dismutase

*Lactobacillus fermentum* ME-3 has a Mn-SOD activity determined by electrophoresis. For determining the SOD type *L. fermentum* ME-3 cell-free extract (30 μg protein) was separated on 10% not-denaturated polyamide-acrylic gel. SOD isoenzyme was determined by influencing this gel with 15 mM $H_2O_2$, after which the SOD activity persisted. Explanation: $H_2O_2$ inhibits Fe-SOD, but does not inhibit Mn-SOD. This proves that *Lactobacillus fermentum* ME-3 has Mn-SOD activity.

The strain *Lactobacillus fermentum* ME-3 showes a high TAA (total antioxidative activity) value in a lipid environment on the basis of a linolenic acid test, also a high TAS (total antioxidative status) value in a hydrate environment (Randox kit, UK). In Table 3, data of the anti-oxidative strain *Lactobacillus fermentum* E-338-1 is added for comparison (Table 3).

The cells and lysates of the strain *Lactobacillus fermentum* ME-3 catch hydroxyl radicals, this has been proven by the terephthalic acid method (27%±5%). 15 mM of reduced glutathione was used for comparison as a well-known scavenger of hydroxyl radicals (84±4.6%). *Lactobacillus fermentum* ME-3 survived in a highly oxidative $H_2O_2$ environment.

Re-cultivation of the lyophilised culture kept in room temperature for a long time proved the viability of the strain and the persistence of properties. This ensures that the lyophilised strain of *Lactobacillus fermentum* ME-3 could be used as a non-comestible product in a scheme of functional food.

BEST MODE FOR CARRYING OUT THE INVENTION

An example of the preparation of a yoghurt with highly anti-oxidative properties based on the strain *Lactobacillus fermentum* ME-3 and the trial of consuming the yoghurt by healthy volunteers.

*Lactobacillus fermentum* ME-3 pure culture in 0.15% MRS-agar is used for producing the yoghurt, additionally the pure cultures of *Lactobacillus plantarum* and *Lactobacillus buchneri* are seeded into fresh goat milk autoclaved for 20 min at 110° C. Three cultures of these strains of lactobacilli are mixed in equal proportions together with 2% of *Streptococcus thermophilus* and are added in 0.2% of content into autoclaved goat milk.

*Lactobacillus fermentum* ME-3 with strains of lactobacilli and streptococci will guarantee tasty and highly anti-oxidative yoghurt (Table 4).

TABLE 4

The anti-oxidative activity of *Lactobacillus fermentum* ME-3 pure culture and probiotic yoghurt

| Strain | Total anti-oxidative activity (TAA %) | |
| --- | --- | --- |
| | Cells | Yoghurt |
| *Lactobacillus fermentum* ME-3 | 29 | 70 |

In tables 5 and 6, the changes of the intestinal micro-flora and indices of oxidative stress of blood sera of healthy volunteers are shown before and after taking the probiotic goat milk yoghurt during 3 weeks. These changes prove the anti-oxidative (incl. anti-atherogenic) effect on human organism.

Even a higher total anti-oxidative activity of goat milk yoghurt compared with the total anti-oxidative activity of intact microbial cells of *Lactobacillus fermentum* ME-3 is shown in table 5.

Additive microbial strains ensure the standard acidity and consistence of yoghurt.

TABLE 5

The changes of intestinal micro-flora of healthy volunteers (n = 16) before and after consuming probiotic goat milk yoghurt during 3 weeks

| | Before | | After | |
| --- | --- | --- | --- | --- |
| | Persons colonised | Lactoflora ratio (%) | Persons colonised | Lactoflora ratio (%) |
| Consuming goat milk yoghurt (n = 16 persons) | | | | |
| *L. fermentum* | 4* | 0.7–5.77 | 16* | 0.5–49.9# |

TABLE 5-continued

The changes of intestinal micro-flora of healthy volunteers (n = 16) before and after consuming probiotic goat milk yoghurt during 3 weeks

| | Before | | After | |
| --- | --- | --- | --- | --- |
| | Persons colonised | Lactoflora ratio (%) | Persons colonised | Lactoflora ratio (%) |
| Taking goat milk (n = 4 persons) | | | | |
| *L. fermentum* | 0 | 0 | 1 | 0–32.9 |

Statistically significant increase:
*The Fisher Exact Test showed the difference of counts in persons colonised with *Lactobacillus fermentum* ME-3 p < 0.0015;
The Mann-Whitney Rank Sum Test showed the difference of relative share of *Lactobacillus fermentum* ME-3 in lactoflora. Therefore, after consuming yoghurt in 3 weeks the microbe was present in the intestinal tract of all volunteers and the Lactobacillus sp. count was remarkably increased.

TABLE 6

The indices of oxidative stress of blood sera of volunteers (n = 16) before and after consuming probiotic goat milk yoghurt during 3 weeks

| Properties | Standard degree | Blood sera before trial | Blood trial after trial | Increase |
| --- | --- | --- | --- | --- |
| TAA (LA-test, %) | 36 ± 4.5 | 38 ± 3.5 | 45 ± 3.4 | 16% |
| TAS, mmol/L | 1.2 ± 0.2 | 0.82 ± 0.14 | 1.14 ± 0.08 | 29% |
| Glutathione red-ox ratio (GSSG/GSH) | 0.17 ± 0.08 | 0.15 ± 0.01 | 0.11 ± 0.035 | −32% |
| LDL lag-phase (time of resistance) | >30 min | 41 ± 7.9 | 46 ± 8.6 | 11% |
| Basic value of diene conjugates (value of extinction) | <0.3 | 0.27 ± 0.06 | 0.23 ± 0.06 | −15% |
| Ox LDL (U/L) | >127 | 98 ± 12 | 81 ± 19 | −18% |

Explanations:
LA-test—linolenic acid test;
TAA—total anti-oxidative activity;
TAS—total anti-oxidative status;
GSSG—oxidized glutathione;
GSH—reduced glutathione;
GSSG/GSH—glutathione red-ox ratio,
ox LDL—oxidized low-density lipoproteins.

Thus all parameters determined in the blood sera of healthy volunteers changed beneficially during the 3-week yoghurt trial.

The application of the invention is not limited to the above-described example of achievement. In the range of the patent claim, some other variants of use are possible, for example the production of probiotic cheese and other milk products.

Statement

The aim of present invention is to offer a strain of microorganism as a novel anti-microbial and anti-oxidative probiotic for use in pharmaceutical and food industry, also in medicine as an antibiotic resistant preparation for prophylaxis and treatment of gastrointestinal and uroinfections, also against oxidative stress (P.3, line 33-35, P.4, line 1-3)

Concerning the antimicrobial activity (bacteriostatic influence) of the object of invention, the strain *Lactobacillus*

*fermentum* ME-3 expresses anti-microbial effect beside others on *Shigella sonnei, Salmonella typhimurium ja Helicobacter pylori* strains (Page 6, line 21-25; Page 7, Table 2). In addition, the property of *Lactobacillus fermentum* ME-3 to kill the food borne pathogens in milk (bacteriocidic effect) is firstly described (Page 7, Table 2 and line 6-11).

The innate resistance of *Lactobacillus fermentum* ME-3 against antimicrobial preparations (TMP-SMX, ofloxacin, aztreonam, cefoxitin and metronidazole) allows to use it as a preparation accompanying antibiotic treatment in case of gastrointestinal and uroinfections (Page 7, line 17-19; Page 8, line 1-3). This property has not been described elsewhere before.

The unique carbohydrate profile of the cell wall of *Lactobacillus fermentum* ME-3 enables to prevent the adhesion of uropathogenic *Escherichia coli* to the epithelial cells of the upper urinary tract, a property that makes our strain applicable in the prophylaxis of urinary tract infections (Page 8, line 5-26)and has never been described before.

Concerning the antioxidative activity of the strain *Lactobacillus fermentum* ME-3 as the object of the present invention the different specific, principal and novel parameters were firstly described like expression of MnSOD, high-grade total antioxidative status (TAS, verified by internationally accepted method), principal parametres of glutathione (a signal molecule and central cellular antioxidant) system and the value of glutathione redox ratio (Page, 9 Table 3; Page 10, line 1-11, 15-19, 23-26).

Any antioxidativity (including antiatherogenicity) parameters found in human trials (in vivo trials) were not made public elsewhere. Therefore, only in this invention, an influence of consumption of ME-3 on human blood sera specific indices was described (Page 13-14, Table 6) and disclosed the appropriate numerical values. Actually, considering mainly these parameters (significant increase of TAS and oxygen resistance of LDL, lowering the level of oxidized LDL and its diene conjugates altogether indicate improvement of systemic antioxidativity and also significant lowering of cellular oxidative stress) it can be claimed that strain *Lactobacillus fermentum* ME-3 is a novel antioxidative (anti-atherogenic) probiotic (Page 11, line 25-30).

The persistence of the novel strain in gastrointestinal tract after consumption and the beneficial influence on the composition of the intestinal lactobacilli are described for the first time (Page 12, Table 5, line 14-22).

Thus the strain of microorganism *Lactobacillus fermentum* ME-3(DSM 14241) figures a novel antimirobial and antioxidative (anti-atherogenic) probiotic for use in pharmacy and food industry, and in medicine as a preparation resistant to some antimicrobials useful for the prophylaxis and as a preparation accompanying antibiotic therapy of gastrointestinal and urinary tract infections, also against chronic diseases (incl. atherosclerosis) induced by prolonged high-grade oxidative stress.

The invention claimed is:

1. A method for simultaneously suppressing pathogenic bacteria and enhancing the total anti-oxidative activity (TAA) in a food product, comprising:
    adding *Lactobacillus fermentum* strain ME-3 (DSM-14241) to said food product as a probiotic ingredient; and
    incubating the *Lactobacillus fermentum* strain ME-3 (DSM-14241) with said food product for at least 24-48 hours.

2. The method of claim 1, wherein said food product is a dairy product.

3. The method of claim 2, wherein said dairy product is yogurt, cheese, or milk.

4. The method of claim 1:
    wherein said pathogenic bacteria being suppressed are selected from the group consisting of *Escherichia coli, Shigella sonnei, Helicobacter pylori, Staphylococcus aureus,* and *Salmonella typhimurium*.

5. A method for enhancing the anti-oxidative activity of blood sera, comprising:
    administering a food product containing *Lactobacillus fermentum* strain ME-3 (DSM-14241) to a human, wherein said food product has been incubated with the bacteria for at least 24-48 hours prior to administration to said human;
    wherein said enhancement of the anti-oxidative activity of blood sera comprises increases in the total anti-oxidative activity (TAA), the total anti-oxidative status (TAS), and the lag-phase of low density lipoprotein (LDL) in the blood sera, and decreases in the glutathione redox ratio, the level of oxidized low density lipoprotein (ox-LDL), and the basic value of diene conjugates of said blood sera.

* * * * *